United States Patent [19]

Gnehm et al.

[11] Patent Number: 4,503,237
[45] Date of Patent: Mar. 5, 1985

[54] METHOD FOR THE PRODUCTION OF ACEMETACIN

[75] Inventors: René Gnehm, Küngoldingen; Rolf Weber, Zofingen, both of Switzerland

[73] Assignee: Siegfried Aktiengesellschaft, Zofingen, Switzerland

[21] Appl. No.: 450,507

[22] Filed: Dec. 16, 1982

[30] Foreign Application Priority Data

Dec. 28, 1981 [CH] Switzerland .................. 8306/81

[51] Int. Cl.$^3$ ........................................... C07D 209/28
[52] U.S. Cl. .................................. 548/501; 548/500
[58] Field of Search ........................................ 548/501

[56] References Cited

FOREIGN PATENT DOCUMENTS 1411350 10/1975 United Kingdom .

Primary Examiner—Glennon H. Hollrah
Assistant Examiner—D. B. Springer
Attorney, Agent, or Firm—Jordan and Hamburg

[57] ABSTRACT

1-(4-Chlorobenzoyl)-5-methoxy-2-methyl-3-indole acetic acid as known per se is obtainable by means of a novel and more simple method. This method comprises hydrolizing 1-(4-chlorobenzoyl)-5-methoxy-2-methyl-3-indole acetic acid tetrahydropyranyl ester, which ester is a novel compound. The final product obtained is a valuable drug having antiinflammatory activity.

1 Claim, No Drawings

METHOD FOR THE PRODUCTION OF ACEMETACIN

BACKGROUND OF THE INVENTION

The present invention relates to a process for preparing an indole derivative, namely 1-(p-chlorobenzoyl)-5-methoxy-2-methylindole-3-acetoxyacetic acid. The process substantially follows a sequence of reaction steps known per se and including the esterification of 1-(chlorobenzoyl)-5-methoxy-2-methylindole-acetic acid with a chloroacetic acid derivative carrying a protective group on its carboxyl group followed by splitting off the protective group.

The 1-(p-chlorobenzoyl)-5-methoxy-2-methylindole-3-acetoxyacetic acid, for which the World Health Organization recommends the International Nonproprietary Name acemetacin, is disclosed in German Laying-Open-Specification No. DE 22 34 651 A1 as an antiinflammatory drug representing a valuable modification of 1-(p-chlorobenzoyl)-5-methoxy-2-methylindole-3-acetic acid, which latter is well introduced and used in the therapeutic practice, and for which the International Nonproprietary Name indomethacin is well accepted.

From the above names of both compounds according to systematic nomenclature acemetacin obviously can be understood to be a derivative of indomethacin resulting from the esterification of the carboxyl group of indomethacin with the α-hydroxyl group of glycolic acid.

As is obvious for the expert, such as a direct esterification cannot be carried out in practice; instead, glycolic acid must be replaced by a carboxylic acid carrying on its α-carbon atom especially a chlorine atom instead of the hydroxyl group and a suitable protective group on its carboxy radical the proper choice of the protective group is of paramount importance, since under the reaction conditions used for splitting off this protective group at least the other ester bond of the desired final product is split, too, while additionally other groups or radicals of the quite delicate molecule tend to be modified.

For solving this problem a benzyl radical is used as the protective group in the method disclosed in No. DE 22 34 651 A1. The benzyl radical, when used as a protective group, can be split off with hydrogen ions while simultaneously substantially not effecting the remaining moieties of the molecule.

The aforementioned reference also discloses additional alternative ways for preparing acemetacin which methods do not use indometacin as an intermediate. All these methods, however, have the common feature that the last intermediate in the respective sequence of reaction steps carries a benzyl group protecting the carboxyl group, which benzyl group then must be split off hydrogenolytically in a final reaction step.

The method of hydrogenolytic cleavage, however, implies a considerable technical effort if compared to an ester cleavage via hydrolysis. Also the results obtainable with such cleavage are not really efficient, since under the necessary reaction conditions the chlorine atom of the chlorobenzoyl substituent also is split off, at least partially. In practice, the different methods using hydrogenolytic debenzylation obviously were disadvantageous to such an extend that a few years later a method for producing acemetacin was developed (cf. No. DE 29 43 125 A1) based on a planned and careful synthesis of the indole structure itself, in which method α-(chlorobenzoyl)-4-methoxyphenylhydrazine hydrochloride is reacted with benzyl levulinate to yield the corresponding hydrazone, which in turn is subject to a cyclocondensation splitting off ammonia, and yielding the desired final product having an unprotected carboxyl group.

SUMMARY OF THE INVENTION

In accordance with the present invention there is now provided a process for preparing acemetacin via indomethacin, in which the necessary protective group is a protective group which can be split off by means of a simple hydrolysis allowing for such mild reaction conditions that none of the remaining bonds in the molecule is attacked or is influenced at all so that substantially no side reaction products are formed during this hydrolytic cleavage reaction. According to the present invention the protective group is the 2-tetrahydropyranyl radical.

The method of the invention thus is characterized in that 1-(p-chlorobenzoyl)-5-methoxy-2-methylindole-3-acetoxyacetic acid tetrahydropyranyl ester is subject to a normal acid hydrolysis. For carrying out the hydrolysis reaction acetic acid is especially preferred. The reaction temperature preferably is held below the boiling points of acetic acid, and especially preferably is held in the range from about 40° C. to about 60° C.

DETAILED DESCRIPTION OF THE INVENTION 1-(p-Chlorobenzoyl)-5-methoxy-2-methylindole-3-acetoxyacetic tetrahydropyranyl ester is used as the starting material for carrying out the process of the invention. This tetrahydropyranyl ester is a novel compound. It can be easily prepared by well-known methods, which can be carried out by the expert without any difficulty. For instance, 1-(p-chlorobenzoyl)-5-methoxy-2-methylindole-3-acetic acid can be esterified with tetrahydropyranyl chloroacetate, i.e. with the chloroacetic acid tetrahydropyranyl ester, forming the 1-(p-chlorobenzoyl)-5-methoxy-2-methylindole-3-acetoxyacetic tetrahydropyranyl ester with a yield almost equal to the theoretical one.

The chloroacetic acid tetrahydropyranyl ester is a novel compound, too. As shown in the more detailed description below, this novel chloroacetic acid tetrahydropyranyl ester easily also is obtainable by well known reactions. Nevertheless, for the sake of completeness a method of producing the chloroacetic acid tetrahydropyranyl ester is described in detail in the following examples as the first step in a sequence of reaction steps yielding acemetacin, i.e. 1-(p-chlorobenzoyl)-5-methoxy-2-methylindole-3-acetoxyacetic acid as the desired final product.

The equations showing the preparation of the present compounds are given below:

Formular Flow Chart of Reaction Steps

1st Step

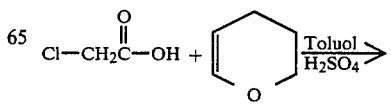

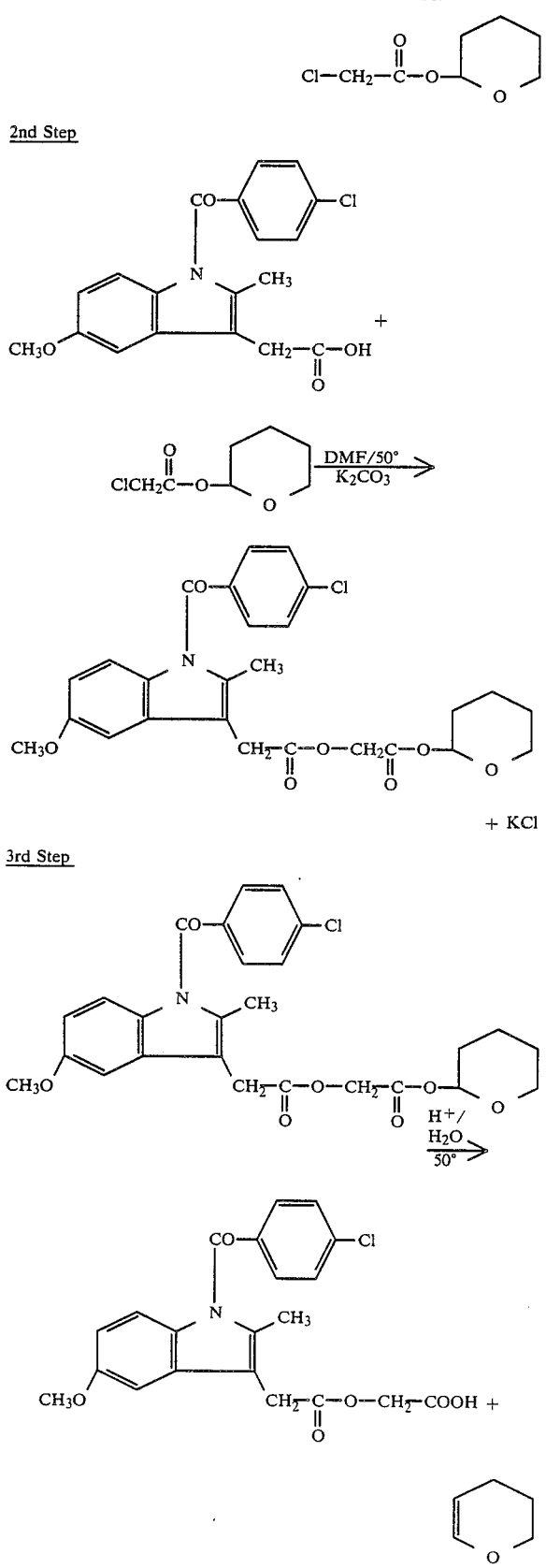

Preparation of Chloroacetic acid tetrahydropyranyl ester:

A mixture of 185 g (2.2 mol) 3,4-dihydro-2H-pyrene, 200 ml toluene and 0.2 ml concentrated sulfuric acid is added dropwise over a period of 15 min at a temperature of 15° C. with a solution of 142 g (1.5 mol) chloroacetic acid in 500 ml toluene. During the addition ice-cooling is provided. After finishing the addition of the chloroacetic acid solution the reaction mixture is stirred 2 hours at room temperature. 15 g anhydrous potassium carbonate are added for stabilizing purposes. The reaction mixture thus stabilized then is evaporated in a rotating evaporator at 45° C. applying the vacuum of a water-jet vacuum pump. Having thus stripped off the lower boiling volatile components a mixture of the tetrahydropyranyl ester and potassium carbonate in an amount of 283 g is obtained as a residue. Based on the chloroacetic acid the yield is 100%.

Prior to using the thus obtained chloroacetic acid tetrahydropyranyl ester as the starting material in the next reaction step the stabilizing agent, in this case potassium carbonate, can (but need not) be separated by filtration.

2nd Reaction Step:

Preparation of 1-(p-Chlorobenzoyl)-5-methoxy-2-methylindole-3-acetoxyacetic acid)tetrahydropyranyl ester (Acemetacintetrahydropyranyl ester):

107.3 g (0.3 mol) of Indomethacin, i.e. 1-(p-chlorobenzoyl)-5-methoxy-2-methylindole-3-acetic acid, are dissolved in 215 ml dimethylformamide and 15 min stirred at 55° C. with 30 g (0.22 mol) anhydrous potassium carbonate. While maintaining this temperature of 55° C. 54 g (0.3 mol) of chloroacetic acid tetrahydrophyranyl ester obtained in step 1 are added dropwise during a period of 20 min. After 1 hour there are added another 18 g (0.1 mol) of tetrahydropyranyl ester, and then stirring is continued for 2.5 h at 55° C. The reaction mixture thus obtained is hydrolized in the 3rd reaction step without separating and recovering the acemetacin-tetrahydropyranyl ester formed.

3rd Reaction Step:

Preparation of Acemetacin (1-(p-chlorobenzoyl-5-methoxy-2-methylindole-3-acetoxyacetic acid):

The reaction mixture obtained in the 2nd reaction step is added 100 ml acetic acid having a concentration of 98% and 30 ml water. The mixture then is stirred 2 hours at a temperature of 50° C. The mixture then is cooled down to 30° C. and diluted with 220 ml water until the solution starts to become turbid. The reaction mixture then is stirred and kept over night at room temperature for the crystallization of crude acemetacin. For the purification of the thus obtained crude acemetacin 122 g of the dried crude material (94% based on the weight of indomethacin used) are re-crystallized in a manner known per se, for instance as disclosed in German reference No. DE 29 43 127 A1, according to which the raw material is dissolved in acetone, from which solution the acemetacin then is precipitated by adding water. After drying the precipitate at 75° C. under a pressure of 8 mbar a purified anhydrous acemetacin is obtained having a melting point of 150°–152° C.

We claim:

1. A process for producing 1-(p-chlorobenzoyl)-5-methoxy-2-methylindole-3-acetoxyacetic acid comprising acid hydrolysis of 1-(p-chlorobenzyol)-5-methoxy-2-methylindole-3-acetoxyacetic acid tetrahydropyranyl ester with diluted acetic acid at a temperature of about 40° C. to about 60° C. and isolation of the desired product.

* * * * *